United States Patent [19]

Steck et al.

[11] 4,186,183

[45] Jan. 29, 1980

[54] LIPOSOME CARRIERS IN CHEMOTHERAPY OF LEISHMANIASIS

[75] Inventors: Edgar A. Steck, Silver Spring, Md.; Carl R. Alving, Washington, D.C.

[73] Assignee: The United States of America as represented by the Secretary of the Army, Washington, D.C.

[21] Appl. No.: 891,257

[22] Filed: Mar. 29, 1978

[51] Int. Cl.² .................... A61K 33/24; A61K 9/50; B01J 13/02
[52] U.S. Cl. ........................................ 424/38; 424/19; 424/131; 252/316
[58] Field of Search ................ 424/19, 38, 131; 252/316

[56] References Cited

PUBLICATIONS

H. Kimelberg, Biochim. et Biophys. Acta, 448 (1976), 531–550.
G. Gregoriadis, N. Eng. J. of Med., 295 (1976) 13, 704–710, The Carrier Potential of Liposomes in Biology and Medicine.
D. Tyrell et al., Biochim. et Biophys. Acta, 457 (1976), 259–302, New Aspects of Liposomes.
Merck Index 9th Edition (1976), #5945, #739.
R. Neal, Chemical Abstracts, 87: 78360h (1977).
N. Ercoli, Chemical Abstracts 66: 93771c (1967).
J. Mikhail et al., Chemical Abstracts 83: 37724d (1975).

*Primary Examiner*—Alton D. Rollins
*Assistant Examiner*—M. C. Eakin
*Attorney, Agent, or Firm*—William C. Gapcynski; Werten F. W. Bellamy; Sherman D. Winters

[57] ABSTRACT

An improved method is provided for the chemotherapy of leishmanial infections. The anti-leishmanial agent is encapsulated within liposomes and the liposome-encapsulated drug is injected into the body. Subject use of a liposome carrier has produced marked enhancement of the effectiveness and duration of anti-leishmanial action of meglumine antimoniate, and of sodium stibogluconate, drugs which are recommended widely for therapy of leishmaniasis.

18 Claims, 1 Drawing Figure

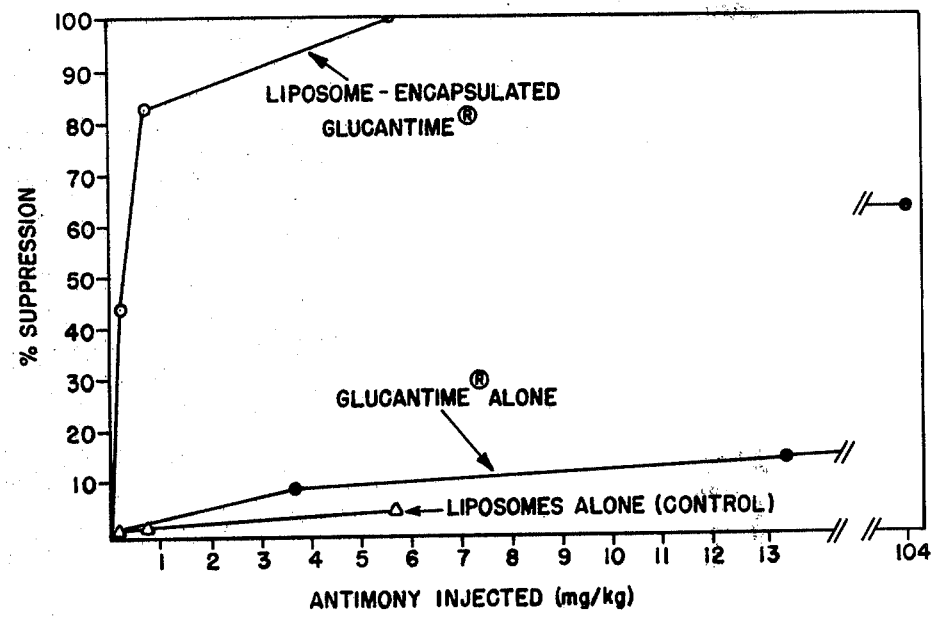

LIPOSOME CARRIERS IN CHEMOTHERAPY OF LEISHMANIASIS

The invention described herein may be manufactured and used by or for the Government for governmental purposes without payment of any royalty thereon.

BACKGROUND OF THE INVENTION

Leishmania are representative of hemoflagellate protozoa and are intracellular parasites of mammalian tissues. The organisms are highly successful in their ability to grow and multiply in tissues of the reticuloendothelial system. It is remarkable that these are the very tissues of the vertebrate host which are ordinarily responsible for hostile reactions to invading foreign organisms. In the reticuloendothelial system, the parasites lie within the host macrophage for at least part of their life cycle. Fusion of host cell secondary lysosomes with the parasitophorous vacuoles apparently occurs without preventing subsequent multiplication of the Leishmania. Such fusion may provide means for access for nutrients to the parasite, but also exposes the parasite to host antibodies and lysosomal enzymes. Despite the potentially hostile intracellular environment, the organisms survive and multiply within the host macrophages. The consequences of leishmanial invasion of the reticuloendothelial system are highly dependent upon a complex interplay of parasite strains and cellular immune responses of the vertebrate host. In man, the result of successful invasion of the spleen and liver most frequently is death. Such infections with *Leishmania donovani*, and other leishmanial strains, are transmitted by the bite of an infected sandfly. Scarring of the skin may be the sole manifestation of infection with *Leishmania tropica* and allied dermatotropic organisms (as, *Leishmania aethiopica, L. mexicana, L. peruviana,* and *L. guyanensis*). Intermediate in severity are invasions of muco-cutaneous tissues by *Leishmania braziliensis*. There are considerable differences among various animals in their response to leishmanial infections; however, a satisfactory animal model for laboratory trials has been found in *Leishmania donovani* infections in the golden hamster.

Relatively few drugs have been found effective against leishmanial disease in man. Antimony drugs are a mainstay for treatment despite evaluation of diverse types both in the laboratory and in clinical trials. Pentavalent compounds of antimony are better tolerated than trivalent antimonials, yet severe toxic side effects may occur, in particular among poorly nourished patients. Toxicity of such drugs may affect the liver (hepatitis), kidneys (nephritis), or the heart (myocarditis). Of these toxic effects, myocarditis is the greatest and most common problem.

Liposomes are defined as closed vesicles, or sacs, which contain phospholipids (examples of which are lecithin and sphingomyelin) and which may contain other lipids (examples of which are cholesterol and other sterols or steroids; charged lipids such as dicetyl phosphate and octadecylamine; glycolipids; and also lipid-soluble vitamins). When shaken in the presence of water, with the water being at least 50% (w/w) compared to phospholipid, the lipid mixture is formed into discrete particles consisting of concentric spherical shells of lipid bilayer membranes which are separated by aqueous interspaces; these are referred to as multilamellar liposomes (MLL). Upon sonication, the MLL are converted to small unilamellar liposomes (ULL). In 1965, it was demonstrated that the MLL vesicle membranes were completely closed and did not allow escape of a marker compound present in the aqueous interspaces; similar properties later were found for ULL.

Numerous studies have shown that liposomes, upon injection into animals and man, are taken up rapidly by cells, and intra-cellular lysosomes, of the reticuloendothelial system, particularly those in the liver. Because of the relative impermeability of liposomes, and speedy removal of them from the circulatory system, substances in the aqueous interspaces of liposomes remain concentrated and are unexposed to plasma. These characteristics of liposomes suggested that they might have a potential for application as carriers for anti-leishmanial agents, particularly antimonial drugs. The cells and tissues in which the liposomes are readily taken up are the very locations in which the Leishmania organisms predominantly reside, thus raising the possibility that liposomes might carry concentrated doses of antimonial agents directly to organisms residing within reticuloendothelial cells of the spleen and liver. Not only would the drugs be directed more effectively to tissues and cells harboring the obligate intra-cellular Leishmania, but also the encapsulated drugs would have decreased liability for producing toxic side-effects through exposure to blood. Moreover, there would be strong probability for prolonged effectiveness of the drug through slow biodegradation of the multilamellar membrane structure of the liposomes. The characteristics of liposomes suggest their suitability as carrier for other antiparasitic agents.

SUMMARY OF THE INVENTION

The present invention relates to a novel technique in treatment of leishmaniasis, consisting in the incorporation of an anti-leishmanial drug into liposomes, and introduction of the "encapsulated" agent into the body of an infected mammal. By this procedure, the effectiveness and duration of action are prolonged, and also drug toxicity is decreased. As specific embodiment of the invention, the use of meglumine antimoniate and of sodium stibogluconate in liposome carriers has been found to provide improved therapy of leishmaniasis due to increased effectiveness, prolonged duration of action, and lessened liability to toxicity of the drug.

Further aspects of the present invention will become apparent upon assessment of the detailed description of the specific embodiments of the novel approach to therapy of leishmanial infections.

DETAILED DESCRIPTION OF THE INVENTION

Meglumine antimoniate and sodium stibogluconate are well known agents for treatment of leishmaniasis in man: Merck Index, Ninth Edition (1976), entry 5945, page 793 and entry 739, page 96; and Progress in Drug Research (E. Jucker, editor), volume 18, The Leishmaniases by E. A. Steck, page 289 [Birkhäuser Verlag, Basel, 1974]. It has now been found that each of the two antimonial drugs can be encapsulated in liposomes. This was effected by drying a thin film of a lipid mixture and introducing an aqueous solution of meglumine antimoniate or of sodium stibogluconate in such manner as to produce liposomes containing the drug. The design of the carrier system for introducing the anti-leishmanial agent was proven to provide markedly enhanced effectiveness of the drug against *Leishmania donovani* infections in a model test system.

EXAMPLES

The herein offered examples provide methods for illustrating, without any implied limitation, the practice of this invention in the treatment of leishmanial infections.

Representative phospholipids which may be used in making the liposomes include lecithin, $\beta$, $\gamma$-dipalmitoyl-$\alpha$-lecithin (as well as related $\beta$, $\gamma$-disubstituted $\alpha$-phosphatidyl choline types), sphingomyelin, phosphatidylserine, phosphatidic acid, and the like. The steroidal component used conveniently in liposome preparation could be cholesterol, coprostanol, cholestanol, cholestanone, and the like. The charged component was selected from readily accessible amphipathic compounds such as dicetyl phosphate, dilauryl phosphate, stearylamine, hexadecylamine, or the like to afford negative or positive charge to the liposomes.

All temperatures not otherwise indicated are in degrees Celsius (°C.). All parts or percentages are given by weight.

Materials

For convenience in preparation of liposomes, stock solutions of phospholipids, cholesterol, and charged component were prepared in chloroform and stored at $-20°$. Commercial normal saline for intravenous injections was the 0.154 M sodium chloride solution here used. Meglumine antimoniate was a commercial sample of Glucantime ® and sodium stibogluconate was a sample of Pentostam ® obtained from the manufacturer. Duplicate antimony determinations were done on the sample as used. Values found were 25.49% and 25.62% antimony in the case of meglumine antimoniate, and 25.93% and 26.13% antimony were assays in the instance of sodium stibogluconate.

Methods

Assessment of anti-leishmanial effects was done in a model test system based on work of Hanson, et al. [Intl. J. Parasitol., 7. 443–447 (1977)].

Male golden hamsters (*Mesocricetus auratus*), weighing approximately 50–60 gm and the Khartoum strain of *Leishmania donovani* were used in this work. Suspensions of amastigotes for the inoculation of experimental hamsters were prepared by grinding heavily infected hamster spleens in Hanks' balanced salt solution in a Ten Broeck tissue grinder and diluting the suspension to contain $10^7$ amastigotes per 0.2 ml, the amount inoculated into each hamster via the intra-cardial route. Administration of the drug was initiated at selected intervals (3 days, or 10 days, or 17 days) after infection and continued once daily for 4 days. One day after halt of therapy, the hamsters were weighed, killed, their livers removed and weighed. Liver impressions were prepared, stained with Giemsa's stain and the ratio of the number of amastigotes per host liver cell nucleus determined.

In preparation for the initiation of therapy, the hamsters were weighed and apportioned into groups of 6 to 11. Solid standard compound, meglumine antimoniate, was prepared in 0.1% Tween ® 80 plus 0.5% hydroxyethylcellulose (HEC-Tween ®) formulation, and administered daily on days 3 through 6 via the intra-cardial route. The reference compound was administered at dose levels of 104, 13, and 3.25 mgm. per kilo per day to the hamsters. Test samples of liposomes containing meglumine antimoniate were injected at presumed dose levels of 104, 13, and 3.25 mg. Sb/kg./day; however, the actual concentration of antimony incorporated into the liposomes (a much smaller amount) was not known at the testing facility. A group of 6 hamsters was the minimum used for each dosage level. The sodium stibogluconate was handled in like manner.

Comparison of the suppressive effects of the various liposome preparations with that of the meglumine antimoniate in HEC-Tween ® was made from parasite densities in the liver of each hamster. The total number of parasites in the liver of each hamster was determined from liver impressions according to the method of Hanson, et al. (loc. cit.).

When the ratio of the number of amastigotes to the number of liver cells had been determined for each hamster in all experimental groups, these data along with initial and final body weights were evaluated with the aid of an IBM 360 computer. A program was devised in which the raw data were accepted by the computer and the total and mean numbers of amastigotes per liver, percent suppression of numbers of amastigotes, and percent body weight change were calculated. Significant tests on the percent suppression of amastigotes were done. The calculations allowed a comparison of the total number of amastigotes in the liver of each hamster receiving the reference preparation or liposome compositions (containing meglumine antimoniate or sodium stibogluconate) with the mean number of amastigotes in the livers of controls.

A comparison of anti-leishmanial activity of each liposome sample was made with the reference formulation of meglumine antimoniate in HEC-Tween ®. This comparison was based upon actual antimony content found in the liposome preparations resulting from incorporation of meglumine antimoniate or of sodium stibogluconate. The drug dosage levels of liposome-encapsulated samples required for a given degree of effect such as 90% suppression ($SD_{90}$) was estimated graphically by plotting on log paper the percent parasite suppression vs. milligrams of compound administered per kilogram body weight of the hamster.

The percentage weight gain or loss of treated animals was used as a crude indication of toxicity. In addition, the hamsters were observed daily for clinical signs of toxicity such as roughened hair coat, nervous disorders and death. At necropsy, gross lesions were noted. All of these criteria were used in assessing any toxicity of the test composition.

The relatively high degree of reproducibility of the screening procedure is apparent in the following data. After 39 weekly experiments, the mean number of amastigotes in the livers of control hamsters was found to be $5.11 \times 10^8$ ($\pm 10^7$, at 95% confidence). Equally good reproducibility was obtained from hamsters receiving 104, 13, or 3.25 mg/kg of the reference compound, meglumine antimoniate. The mean number of amastigotes in the livers of these hamsters were $12.1 \times 10^7$ ($\pm 1.1 \times 10^6$), $1.57 \times 10^8$ ($\pm 11.6 \times 10^6$) and $3.4 \times 10^8$ ($\pm 1.39 \times 10^6$). These represent suppressions of 97.6%, 69.2% and 38.3%, respectively, for the three drug dosage levels.

EXAMPLE 1

Meglumine Antimoniate Encapsulated in Negatively-Charged Liposomes

Chloroform solutions of dipalmitoyl phosphatidylcholine, cholesterol, and dicetyl phosphate were prepared. Portions of each were mixed in such way that there were molar ratios of 2/1.5/0.22. The mixture was placed in a pear-shaped flask, and the solvent removed in vacuo on a rotary evaporator. There resulted an homogeneous film of lipid, which was further dried under high vacuum. To that there was added a small amount of 0.5 mm. glass beads, followed by sufficient aqueous 0.308 M solution of meglumine antimoniate so that the phosphatidylcholine content of the final aqueous dispersion was 10 mM. The liposomes were swollen by shaking for several minutes on a vortex mixer, and then freed of untrapped meglumine antimoniate by diluting in 10 volumes of 0.15 M sodium chloride solution and centrifuging at 20 200 g for 10 min. at 22°. Each pellet was suspended in 0.15 M sodium chloride solution in half of the original aqueous volume. The resulting liposomes were injected into *L. donovani*-infected hamsters.

Analysis of an aliquot of the washed liposomes was done to ascertain the amount of meglumine antimoniate trapped in the vesicles. The liposomes were disrupted and lipids removed by shaking the portion with an equal volume of chloroform. The aqueous phase and water washings of the chloroform layer were combined and subjected to atomic absorption analysis for antimony. It was found that the washed liposome trapped 1.9% to 7% of meglumine antimoniate present in the original swelling solution.

Direct comparison was made of the effects produced in Leishmania-infected hamsters by intracardial administration of meglumine antimoniate (MA) alone and drug incorporated in liposomes. Table 1 shows the results of treatments on infections of various duration. It should be noted that about half of untreated animals would die ordinarily within some 4 weeks of infection with *L. donovani*. The comparison of anti-leishmanial effects of total doses of MA per se (416 mgm/kg) and encapsulated in liposomes (4 mgm/kg) showed that enhanced anti-leishmanial effects of the latter are more noteworthy in the long-standing infections. This has basic practical significance, for cases presented at the clinic are usually of some duration. Thus, Table 1 gives evidence that 17 days post-infection, animals showed 61% suppression of parasitemia when liposome-incorporated MA was administered, whilst only 18% suppression resulted when more than 100 fold dosage of drug alone was given. Data were also assembled in comparison of the effects of meglumine antimoniate (MA) alone, liposome-incorporated MA, and "empty" liposomes (swollen in sodium chloride) on 10-day infections of hamsters with *L. donovani*. Those data form basis of FIG. 1. Calculations from the data of FIG. 1 show that the estimated dose required for 50% suppression of leishmanial infection for meglumine antimoniate, alone, was some 350 times greater than that for the drug entrapped within liposomes.

In this experiment, hamsters had been infected with *L. donovani* for 10 days prior to treatment. The indicated doses of meglumine antimoniate were administered daily for four days. In the control animals there were given equivalent volumes of liposomes which had been swollen in normal saline solution, rather than liposomes which had been swollen in 0.308 M meglumine antimoniate.

Table 1

| Influence of Length of Infection on Efficacy of Treatment | | | |
|---|---|---|---|
| | Time between infection and start of treatment (days) | | |
| | 3 | 10 | 17 |
| Treatment used | % Suppression | | |
| Liposomes plus meglumine antimoniate (1 mg/kg/day for 4 days) | 99.8 | 82.8 | 61.3 |
| Meglumine antimoniate alone (104 mg/kg/day for 4 days) | 99.8 | 63.7 | 18 |

It is well known that conventional therapy with antimonial drugs may be hazardous to the patient through diverse toxic side effects. Encapsulation of meglumine antimoniate in liposomes provides a novel means for preventing untoward effects in two ways. Rapid uptake of liposomes by cells, especially those of the reticuloendothelial system (parasitized by Leishmania), diminishes exposure of other tissues to the drug within the liposomes. Further, based upon results in the animal model, less than 0.3% of an ordinary therapeutic dose may be used for equivalent therapy.

EXAMPLES 2 THROUGH 12

Meglumine Antimoniate Encapsulated in Liposomes

The procedure described in Example 1 was following using other lipid mixtures for incorporating meglumine antimoniate (MA), as outlined in Table 2. In the preparation of neutral liposomes, the phospholipid and cholesterol were used in a 2:1.5 ratio. The charged liposomes were made with 2:1.5:0.22 ratio of phospholipid, cholesterol, and positively or negatively charged lipid. As shown in Table 2, variable amounts of drug were incorporated into liposomes. The effectiveness of the liposome-encapsulated MA was determined in direct comparison with drug in the standard vehicle and liposomes formed by swelling the mixture in 0.154 M sodium chloride solution.

Table 2

| | Liposome-Encapsulated Meglumine Antimoniate | | | | |
|---|---|---|---|---|---|
| | | | % Suppression at PDL, mg/kg/day[d] | | |
| Example | Composition of Liposomes[a] | Correction Factor[b] | 104 | 13 | 3.25 |
| 2 | DMPC/Chol/DCP (2/1.5/0.22) | 0.07 | 100 | 99.2 | 90.0 |
| 3 | DMPC/Chol/SA (2/1.5/0.22) | 0.039 | 99.96 | 93.9 | 71.1 |
| 4 | DMPC/Chol (2/1.5) | 0.023 | 99.9 | 68.6 | 49 |
| 5 | DSPC/Chol/DCP (2/1.5/0.22) | 0.043 | 99.96 | 96.6 | 79.4 |
| 6 | Egg PC/Chol/DCP (2/1.5/0.22) | 0.019 | 98.2 | 86.4 | 42.2 |
| 7 | Egg PC/Chol/SA (2/1.5/0.22) | 0.033 | 44.4 | (e) | (e) |
| 8 | Egg PC/Chol (2/1.5) | 0.0375 | 82.1 | 55.7 | 61 |
| 9 | SM/Chol/DCP (2/1.5/0.22) | 0.032 | 97.3 | 49.7 | 0 |
| 10 | SM/Chol/SA (2/1.5/0.22) | 0.024 | 98 | 67.5 | 63 |

Table 2-continued

| | | Liposome-Encapsulated Meglumine Antimoniate | | | |
|---|---|---|---|---|---|
| | | | % Suppression at PDL, mg/kg/day[d] | | |
| Example | Composition of Liposomes[a] | Correction Factor[b] | 104 | 13 | 3.25 |
| 11 | DMPC/Chol/DPPA (2/1.5/0.22) | (c) | 100 | 90.3 | 67.2 |
| 12 | DMPC/Chol/PS (2/1.5/0.22) | (c) | 99.3 | 91.6 | (e) |

Footnotes to Table 2
[a]Legend: DMPC, dimyristoyl phosphatidylcholine; DPPC, dipalmitoyl phosphatidylcholine; DSPC, distearoyl phosphatidylcholine; Egg PC, egg phosphatidylcholine; SM, sphingomyelin; SA, stearylamine; Chol, cholesterol; DCP, dicetyl phosphate; DPPA, dipalmitoyl phosphatidic acid; PS, phosphatidylserine. Molar ratios of components given parenthetically. Swollen in 0.308 M meglumine antimoniate. The hamsters had been infected 24 days prior to starting therapy.
[b]Based upon assays (by atomic absorption) of antimony content of liposomes. IF 100% incorporation, antimony content would have been the same as that of meglumine antimoniate (correction factor = 1). Actual extent of incorporation was usually 2.5% to 7% of drug available in swelling solution. Cf. footnote (d).
(c) Not determined.
[d]Presumed dose levels (PDL) are those administered without knowledge of actual extent of drug incorporation in liposomes. Actual doses were the PDL, given in 4 doses, multiplied by the correction factor [footnote (b)] obtained from data on actual extent of meglumine antimoniate present in the individual preparations.
(e) All animals died.

control liposomes formed by swelling of the phospholipid mixture in sodium chloride solution.

Table 4

| | | Liposome-Encapsulated Sodium Stibogluconate | | | |
|---|---|---|---|---|---|
| | | | % Suppression at PDL, mg/kg/day[c] | | |
| Example | Composition of Liposomes[a] | Correction Factor[b] | 104 | 13 | 3.25 |
| 19 | DMPC/Chol/DCP (2/1.5/0.22) | 0.036 | 99.7 | 85.7 | 32.5 |
| 20 | DMPC/Chol/SA (2/1.5/0.22) | 0.042 | 99.9 | 63.4 | 10.2 |
| 21 | DMPC/Chol (2/1.5) | 0.045 | 99.99 | 90 | 64.9 |

[a]Legend: DMPC, dimyristoyl phosphatidylcholine; Chol, cholesterol; DCP, dicetyl phosphate; SA, stearylamine. Molar ratios of components given parenthetically. swollen in 0.308 M sodium stibogluconate. The animals had been infected for 17 days before starting therapy.
[b]Based upon atomic absorption assays of antimony content of liposomes. If 100% incorporation, antimony content would have been the same as for sodium stibogluconate and the correction factor equal to unity.
[c]Cf. Table 2, footnote (d).

EXAMPLES 13 THROUGH 18

Influence of Drug Concentration on Incorporation in Liposomes

A procedure analogous to that described in Example 1 was followed with varying concentrations of meglumine antimoniate solution being used to swell the liposomes. Table 3 shows the advantage of concentrations approximately 0.3 molar with respect to drug.

TABLE 3

| | Influence of Meglumine Antimoniate Concentration upon Incorporation in Liposomes[a] | | |
|---|---|---|---|
| Example | Meglumine Antimoniate in Swelling Sol'n (mg) | % Incorp. of Sb into Liposomes | Total Incorp. of Meglumine Antimoniate (mg) |
| 13 | 56.4 | 4.3 | 2.42 |
| 14 | 113 | 6.8 | 7.7 |
| 15 | 146 | 4.3 | 6.3 |
| 16 | 180 | 4.6 | 8.3 |
| 17 | 225 | 3.6 | 8.1 |
| 18 | 339 | 2.2 | 7.5 |

Footnote to Table 3
[a]Liposomes were prepared by swelling a mixture of dipalmitoylphosphatidylcholine, cholesterol, and dicetyl phosphate(molar ratios, 2/1.5/0.22) in meglumine antimoniate solutions.

EXAMPLES 19 THROUGH 21

Sodium Stibogluconate Encapsulated in Liposomes

The incorporation of sodium stibogluconate into liposomes was accomplished by a procedure entirely analogous to that employed for meglumine antimoniate in Examples 2, 3, and 4. Table 4 shows the results of these trials. As in Examples involving use of meglumine antimoniate, comparison was made of liposome-incorporated sodium stibogluconate with drug per se and

We claim:
1. The product prepared by a process for encapsulating an antimonial drug with liposomes comprising the steps of:
   a. drying a lipid mixture to form a dry film;
   b. wetting the lipid film with an aqueous solution of the antimonial drug;
   c. mixing the aqueous solution of antimonial drug and lipid film to form a suspension of antimonial drug encapsulated by liposomes;
   d. separating the liposome-encapsulated drug; and
   e. washing the liposome-encapsulated antimonial drug to remove substantially all nonencapsulated antimonial drug therefrom.

2. A method for the chemotherapy treatment of leishmaniasis by administering to an infected animal a leishmanicidally effective amount of liposome-encapsulated antimonial drug of claim 1.

3. The method of claim 2 wherein the lipid mixture in step (a) consists of a phospholipid and cholesterol.

4. The method of claim 2 wherein the lipid mixture in step (a) consists of a phospholipid, cholesterol, and a charged amphipathic compound.

5. The method of claim 4 wherein the phospholipid is selected from the group consisting of a phosphatidyl choline derivative, a glycerophosphatide, a lysophosphatide, sphingomyclin, and mixtures thereof.

6. The method of claim 4 wherein the amphipathic compound is selected from the group consisting of a di (alkyl) phosphate, a phosphatidic acid and a phosphatidyl serine.

7. The method of claim 4 wherein the amphipathic compound is selected from the group consisting of dicetyl phosphate, dilauryl phosphate, stearylamine and hexadecylamine.

8. The method of claim 2 wherein the antimonial drug is meglumine antimoniate.

9. The method of claim 2 wherein the antimonial drug is sodium stibogluconate.

10. The method of claim 3 wherein the antimonial drug is meglumine antimoniate.

11. The method of claim 3 wherein the antimonial drug is sodium stibogluconate.

12. The method of claim 4 wherein the antimonial drug is meglumine antimoniate.

13. The method of claim 4 wherein the antimonial drug is sodium stibogluconate.

14. The method of claim 5 wherein the antimonial drug is meglumine antimoniate.

15. The method of claim 5 wherein the antimonial drug is sodium stibogluconate.

16. The method of claim 7 wherein the charged amphipathic lipid is selected from the group consisting of stearylamine and hexadecylamine.

17. The method of claim 7 wherein the charged amphipathic compound is selected from the group consisting of dicetyl phosphate, dilauryl phosphate, phosphatidyl serine, and phosphatidic acid.

18. A composition for the chemotherapy treatment of leishmaniasis comprising a leishmanicidally effective amount of a liposome-encapsulated antimonial drug.

* * * * *